US007001386B2

(12) United States Patent
Sohngen et al.

(10) Patent No.: US 7,001,386 B2
(45) Date of Patent: Feb. 21, 2006

(54) INTRAMEDULLARY NAIL FOR LONG BONE FRACTURES (75) Inventors: Gary Sohngen, San Pedro, CA (US); Barry Hubbard, Sandy, UT (US)

(73) Assignee: Advanced Orthopaedic Solutions, Inc., San Pedro, CA (US)

( * ) Notice: Subject to any disclaimer, the term of this patent is extended or adjusted under 35 U.S.C. 154(b) by 39 days.

(21) Appl. No.: 10/624,463

(22) Filed: Jul. 21, 2003

(65) Prior Publication Data
US 2005/0055023 A1 Mar. 10, 2005

Related U.S. Application Data (60) Provisional application No. 60/398,294, filed on Jul. 23, 2002.

(51) Int. Cl.
A61B 17/58 (2006.01)
(52) U.S. Cl. ...................................... 606/62
(58) Field of Classification Search ............ 606/62–66
See application file for complete search history.

(56) References Cited

U.S. PATENT DOCUMENTS

| 3,846,846 A | * | 11/1974 | Fischer ................... 623/23.18 |
| 4,262,665 A | * | 4/1981 | Roalstad et al. ............. 606/62 |
| 4,622,959 A | | 11/1986 | Marcus |
| 4,640,271 A | * | 2/1987 | Lower ......................... 606/65 |
| 4,733,654 A | | 3/1988 | Marino |
| 4,827,917 A | | 5/1989 | Brumfield |
| 5,167,663 A | | 12/1992 | Brumfield |
| 5,312,406 A | | 5/1994 | Brumfield |
| 5,472,444 A | | 12/1995 | Huebner et al. |
| 5,562,666 A | | 10/1996 | Brumfield |
| 5,743,912 A | * | 4/1998 | Lahille et al. ................ 606/65 |
| 6,010,506 A | | 1/2000 | Gosney et al. |
| 6,106,528 A | | 8/2000 | Durham et al. |
| 6,126,661 A | | 10/2000 | Faccioli et al. |
| 6,197,029 B1 | | 3/2001 | Fujimori et al. |
| 6,228,086 B1 | | 5/2001 | Wahl et al. |
| 6,235,031 B1 | | 5/2001 | Hodgeman et al. |
| 6,296,645 B1 | | 10/2001 | Hover et al. |

* cited by examiner

Primary Examiner—Eduardo C. Robert
Assistant Examiner—Annette Reimers
(74) Attorney, Agent, or Firm—Clayton, Howarth & Cannon, P.C.

(57) ABSTRACT

An intramedullary nail for treating long bone fractures. The nail includes a proximal portion that may have a plurality of segments. The segments may be rotatable 360 degrees about a longitudinal axis of the nail such that the position of bone screw openings in the segments can be adjusted to a desired orientation. Locking rings or other locking mechanisms may be provided between the segments to lock the segments in place and allow the segments to be unlocked for readjustment of the position of the segments. The bone screw openings may be configured to allow further angular adjustment of the bone screws with respect to the longitudinal axis of the nail. Inserts may be placed within the bone screw openings to support the bone screws in position.

25 Claims, 8 Drawing Sheets

INTRAMEDULLARY NAIL FOR LONG BONE FRACTURES

CROSS-REFERENCE TO RELATED APPLICATIONS

This application claims the benefit of U.S. Provisional Application No. 60/398,294, filed Jul. 23, 2002, which is hereby incorporated by reference herein in its entirety, including but not limited to those portions that specifically appear hereinafter, the incorporation by reference being made with the following exception: In the event that any portion of the above-referenced provisional application is inconsistent with this application, this application supercedes said above-referenced provisional application.

STATEMENT REGARDING FEDERALLY SPONSORED RESEARCH OR DEVELOPMENT

Not Applicable.

BACKGROUND OF THE INVENTION

1. The Field of the Invention

The present invention relates generally to an intramedullary nail for the repair of long bone fractures, and more specifically, to an adjustable nail that allows a surgeon to use a single nail to treat any fracture configuration using different surgical techniques.

2. Description of Related Art

Intramedullary nails are proven devices that provide a temporary fixation means to stabilize a fracture until the fracture heals. The nail is inserted in the marrow canal of the bone and is positioned to span the fracture. The nail is anchored within the bone via bone screws placed through aligned apertures in the nail as received in the bone. The screws are usually inserted in the proximal and distal ends of the nail and the orientation of the screws depends upon the particular fracture configuration and the type of long bone fracture, i.e. femur, tibia, humerus. Thus, different nails are required for different long bone fractures. Many hospitals stock complete nail systems that are only designed to treat specific fractures. Not only does each nail system require different components, many require unique instrumentation systems intended for use with only one type of nail. This results in increased and unnecessary inventory that correspondingly increases the cost to the hospital and patient. Accordingly, it is advantageous to have an intramedullary nail with greater flexibility that allows a surgeon more options to handle a wider range of fractures while streamlining the components necessary to do so. Additionally, the intramedullary nail may be used in joint fusion between long bones.

Intramedullary nails may offer distinct advantaged over other methods of fixation. For example, intramedullary nails may help bones heal faster, with lower rates of infection as compared to other surgical methods of fixation. Moreover, improved early mobilization of limbs having the broken bone may be achieved. One of the significant improvements over other methods of fixation is that intramedullary nails may share loads with the bone, rather that entirely supporting the bone across the fracture site. Because of this, patients may be able to move the broken limb sooner than they would with traditional casting of the bone. This may help maintain more strength of the muscles and prevent frozen joints, where joints become stiff after prolonged casting.

A drawback known in the art of intramedullary nails is the difficulty in providing a nail having receiving openings that are properly positioned to enable treatment of fractured bone fragments in various different configurations. A further drawback known in the art is provided in aligning the bone screws with the openings in the intramedullary nail. For example, longitudinal angular misalignment may occur when the axis of the receiving opening and the axis of the bone screw are at different angles relative to the longitudinal axis of the nail. Similarly, transverse angular misalignment may occur when the axis of the receiving opening and the axis of the bone screw are in the same transverse plane but at different radial positions relative to the longitudinal axis of the nail. Various types of insertion jigs have been proposed to properly align the bone screws with the receiving openings. However, it would be an improvement in the art to provide an intramedullary nail that is adjustable to treat fractured bone fragments having different configurations and which alignment of the receiving openings is facilitated. It would be a further improvement in the art to provide such an intramedullary nail that has adjustable segments that are capable of being locked in place and that can be unlocked to be readjusted. It would be an additional improvement in the art to provide such an intramedullary nail that is simple in design and manufacture.

The prior art is thus characterized by several disadvantages that are addressed by the present invention. The present invention minimizes, and in some aspects eliminates, the above-mentioned failures, and other problems, by utilizing the methods and structural features described herein.

The features and advantages of the invention will be set forth in the description which follows, and in part will be apparent from the description, or may be learned by the practice of the invention without undue experimentation. The features and advantages of the invention may be realized and obtained by means of the instruments and combinations particularly pointed out in the appended claims.

BRIEF DESCRIPTION OF THE DRAWINGS

The features and advantages of the invention will become apparent from a consideration of the subsequent detailed description presented in connection with the accompanying drawings in which.

DETAILED DESCRIPTION OF THE INVENTION

For the purposes of promoting an understanding of the principles in accordance with the invention, reference will now be made to the embodiments illustrated in the drawings and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would normally occur to one skilled in the relevant art and having possession of this disclosure, are to be considered within the scope of the invention claimed.

It must be noted that, as used in this specification and the appended claims, the singular forms "a," "an," and "the" include plural referents unless the context clearly dictates otherwise.

In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps.

Figure 1:
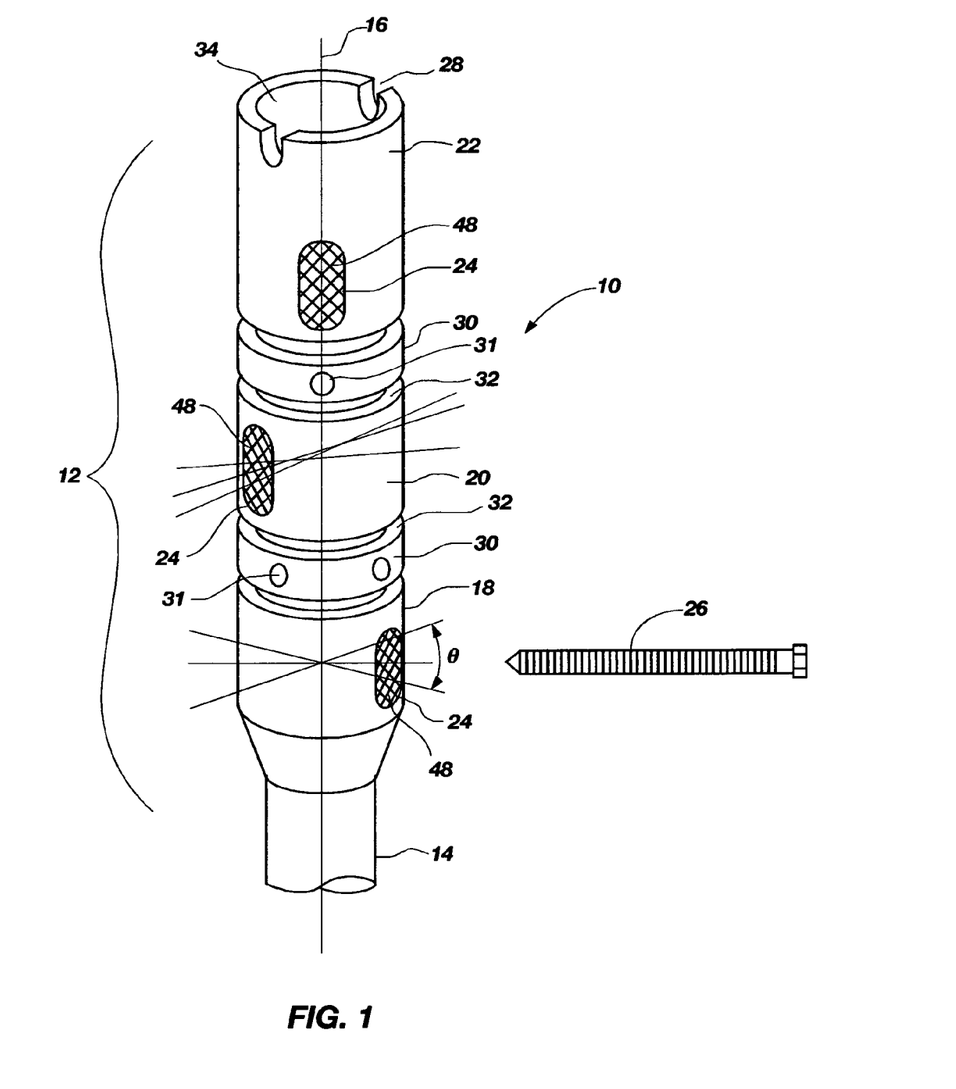
FIG. 1 is a break-away perspective view of an intramedullary nail in accordance with the principles of the present invention.

Referring now to FIG. 1, a break-away perspective view of an intramedullary nail, in accordance with the principles of the present invention, is indicated generally at 10. Intramedullary nail 10 may also sometimes be referred to as a femoral nail. However, it will be appreciated that the nail 10 may be used for the treatment of fractures in various different bones such as the femur, humerus, tibia, and fibula, for example, or any other bone for which nail 10 may provide assistance, within the scope of the present invention.

The intramedullary nail 10 may have an elongate configuration forming a proximal portion 12 and a distal portion 14. The proximal portion 12 and the distal portion 14 may define a longitudinal axis 16 of the nail 10. It will be appreciated that the structure of the distal portion 14 of the nail 10 that is not shown may be formed of any configuration known in the art of intramedullary nails.

The proximal portion 12 may include a first segment 18, a second segment 20, and a third segment 22. It will be appreciated that different numbers of segments may be incorporated into the nail 10 within the scope of the present invention. The first segment 18 may be attached to the distal portion 14 such that the first segment 18 and the distal portion 14 are formed as an integral unit to define a portion of the nail sometimes referred to as the substrate. The second segment 20 and the third segment 22 may be configured to rotate 360 degrees about the longitudinal axis 16 as discussed more fully below.

The first segment 18, the second segment 20 and the third segment 22 may each include a transverse opening 24 for receiving a bone fastener such as a bone screw 26. The bone screw 26 may include any of a variety of bone screws known in the art for fixing intramedullary nails in place. The transverse opening 24 may have a substantially oval shape such that the bone screw 26, which may be much narrower in width than the size of the opening 24, may be angulated or inserted into the transverse opening 24 in a range of angles θ with respect to the longitudinal axis 16. In one embodiment, the transverse opening 24 may be configured to allow the angle θ of the bone screw 26 to vary within a range of approximately fifteen degrees. However, it will be appreciated by those skilled in the art that the transverse opening 24 may be configured to allow the angulation of the bone screw 26 through other ranges of angles θ.

The transverse openings 24 may also include an insert 48 that can be drilled or otherwise penetrated by the bone screw 26 such that the bone screw 26 may be supported in the various angles θ. The insert 48 may be formed of a bioresorbable poly lactic acid (PLA) or high density polyethylene (HDPE) for example, or other suitable material known in the art. It will be appreciated that the nail 10 may be used either with or without the insert 48 within the scope of the present invention. The transverse openings 24 may also be used to allow dynamization of the nail. That is, to allow motion at the fracture site to assist in fracture healing.

The proximal portion 12 of the nail 10 may include locking rings 30 for fastening the segments together. The locking rings 30 may include one or more tool openings 31 for receiving a tool to apply a force to the locking rings 30 or otherwise manipulating the locking rings 30.

Figure 2A:
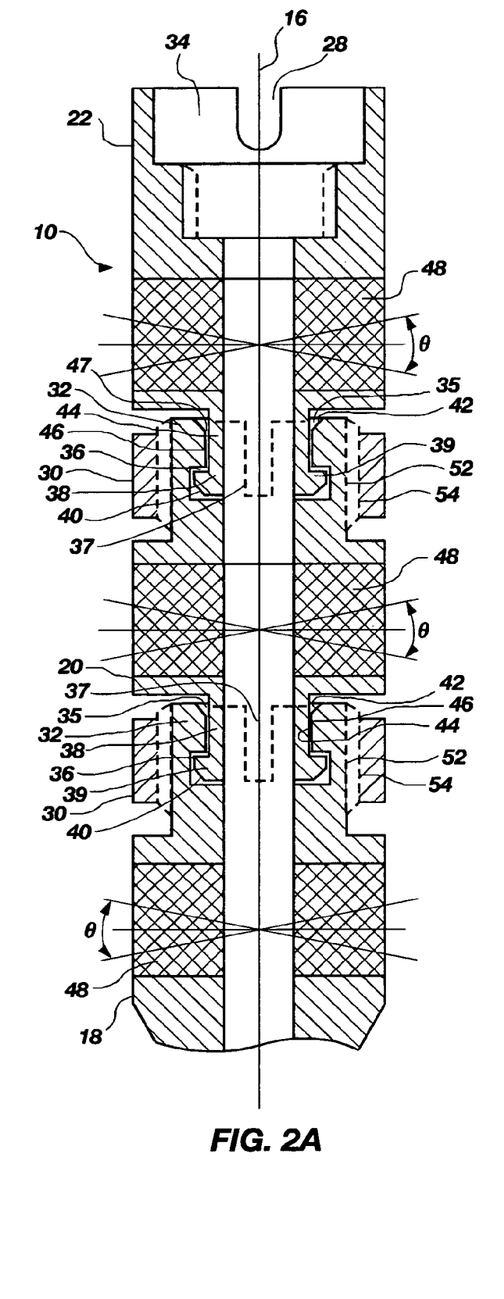
FIG. 2A is a side, cross-sectional break-away view of the intramedullary nail of FIG. 1.

Referring to FIG. 2A a side, cross-sectional break-away view of the intramedullary nail 10 is shown. The nail 10 may include a bore 34 extending along the longitudinal axis 16. The first segment 18 and the second segment 20 may each include a sidewall 32 defining a chamber 35. The chambers 35 may be configured for receiving a connector 38 formed on a distal end of each of the second segment 20 and the third segment 22. The connector 38 may include a ledge 39, and the chamber 35 may include a slot 36 for receiving the ledge 39. The placement of the ledge 39 in the slot 36 functions to prevent the segments from separating and allow the segments to rotate about the longitudinal axis 16. A chamfer 40 may be formed on a distal end of the ledge 39 and an annular portion 42 surrounding the chamber 35 may be tapered to facilitate inserting the connector 38 into the chamber 35. The sidewall 32 surrounding the chamber 35 may include a plurality of slits 37, shown in dashed lines in FIG. 2A. The slits 37 in the sidewalls 32 allow the sidewalls to deflect more easily to assist in inserting the connectors 38 and locking the segments together.

The connector 38 may be held in place within the chamber 35 using the locking rings 30. The connector 38 may have an engagement surface 44 corresponding to a contact surface 46 of the chamber 35. The locking rings 30 may exert a force or circumferential squeeze on the sidewall 32 of the first segment 18 and the second segment 20 in an inward direction toward the axis 16 such that the contact surface 46 of the chamber 35 fastens to the engagement surface 44 of the connector 38. The circumferential squeeze exerted by the locking rings 30 may be created in various ways. For example, the locking rings 30 may have a threaded interior surface 52 having a slightly smaller diameter than a threaded exterior surface 54 of the sidewall 32. The locking ring 30 may be rotated to draw the locking ring 30 over the sidewall 32 and thereby create a threaded squeeze on the sidewall 32. Alternatively, as discussed more fully below in the embodiment of FIGS. 4A and 4B, the locking ring 30 may have an interior surface that is tapered, and/or the exterior surface of the sidewall 32 may be tapered such that when the locking ring 30 is moved axially along the sidewall 32, the locking ring 30 creates a tapered squeeze on the sidewall 32.

In one embodiment of the present invention, the force exerted by the locking rings 30 deflects the contact surface 46 of the chamber 35 inwardly such that the contact surface 46 forms a slight taper. The tapered contact surface 46 may create a taper lock with the connector 38 to lock the segments together. The interaction between the engagement surface 44 of the connector 38 and the contact surface 46 of the chamber 35 may cause the material in one or both of the engagement surface 44 and the contact surface 46 to gall and fuse together to form a cold weld, indicated at 47. In one embodiment of the present invention, the segments may be formed of a titanium material that is known to have properties suitable for galling and providing a good cold weld connection. The engagement surface 44 and/or the contact surface 46 may also include grooves or other forms of machining to assist in the galling of the surfaces to improve the cold weld 47.

In use, the distal portion 14 of the nail 10 may be aligned for proper placement in a fractured bone such that the transverse opening 24 in the first segment 18 is properly oriented. The second segment 20 and the third segment 22 may be rotated 360 degrees with respect to the first segment 18 about the axis 16 such that all of the transverse openings 24 are oriented to enable a bone screw 26 to be placed to capture fractured bone fragments or otherwise to be positioned as desired. Thus, a single nail 10 can be adjusted to a multitude of different configurations to treat bone fractures, whereas numerous prior art nails would be required to offer such a range of treatment configurations. The segments may then be locked in place using the locking rings 30 and the nail 10 may be inserted into a bone. Bone screws 26 may be inserted into the openings 24 with the assistance of external alignment guides or jigs. The position of the bone screws 26 within the openings 24 may be angulated within an angle θ to further orient the bone screws 26 as desired.

Figure 3A:
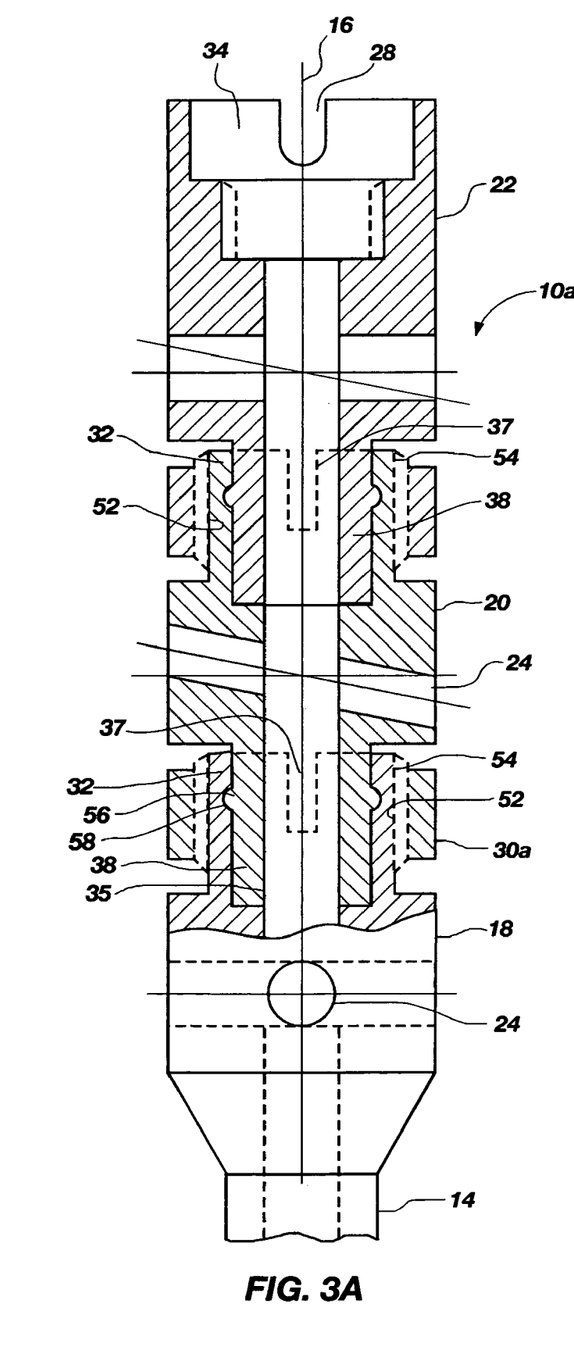
FIG. 3A is a side, cross-sectional break-away view of an alternative embodiment of the intramedullary nail of FIG. 2A.
Figure 3B:
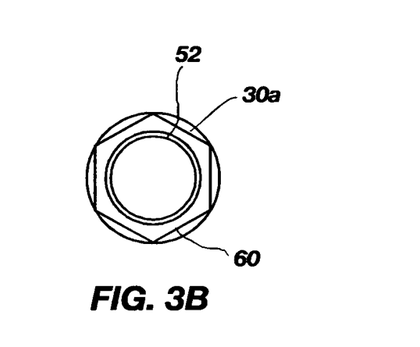
FIG. 3B is a top view of a hexagonal sleeve of the intramedullary nail of FIG. 3A.

Reference will now to made to FIGS. 3A and 3B to describe a second embodiment of the present invention. As previously discussed, the embodiments of the invention illustrated herein are merely exemplary of the possible embodiments of the invention, including that illustrated in FIGS. 3A and 3B.

Figure 2B:
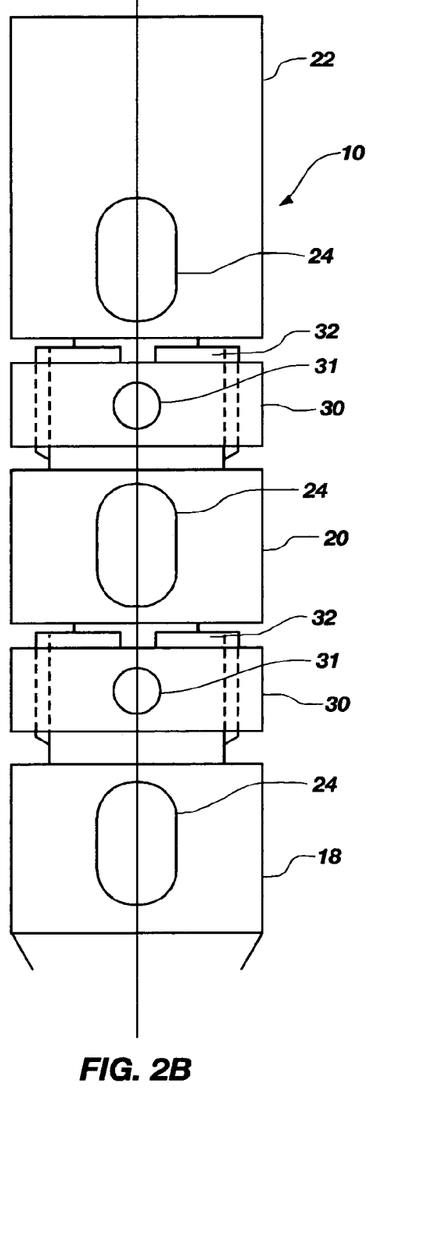
FIG. 2B is a front, break-away view of the intramedullary nail of FIG. 2A.

It will be appreciated that the second embodiment of the invention illustrated in FIGS. 3A and 3B contains many of the same structures represented in FIGS. 1–2, and the new or different structures will be explained to most succinctly explain the additional advantages which come with the embodiments of the invention illustrated in FIGS. 3A and 3B.

The second embodiment of the intramedullary nail 10*a* may include a projection 56 on an exterior surface of the connector 38, and a groove 58 may be provided on the interior surface of the sidewall 32 to further provide an interference fit between the sidewall 32 and the connector 38. It will also be appreciated that the projection 56 may be provided on the sidewall 32, and the groove 58 may be provided on the connector 38 within the scope of the present invention.

The second embodiment of the invention may also include locking rings 30*a* which may function in a similar manner as the threaded locking ring discussed above. Locking rings 30*a* may have a threaded interior surface 52 mating with a threaded exterior surface 54 of the sidewall 32 of the first segment 18 or the second segment 20. The locking rings 30*a* may be sized such that rotation of the locking rings 30*a* may cause the sidewall 32 to thread into the locking ring 30*a* and thereby cause the sidewalls 32 to deflect inward toward the axis 16. The inward movement of the sidewalls 32 may lock the connector 38 within the chamber 35. The locking engagement may be released by rotating the locking ring 30*a* such that the sidewall 32 is removed from the locking ring 30*a*.

The locking ring 30*a* may also have a cross section shaped for applying a torque to the locking ring 30*a*, such as a hexagonal shape 60 shown in FIG. 3B. It will be appreciated that various shapes such as polygonal shapes or knurled surfaces may be used to provide a torque applying surface within the scope of the present invention.

Figure 4A:
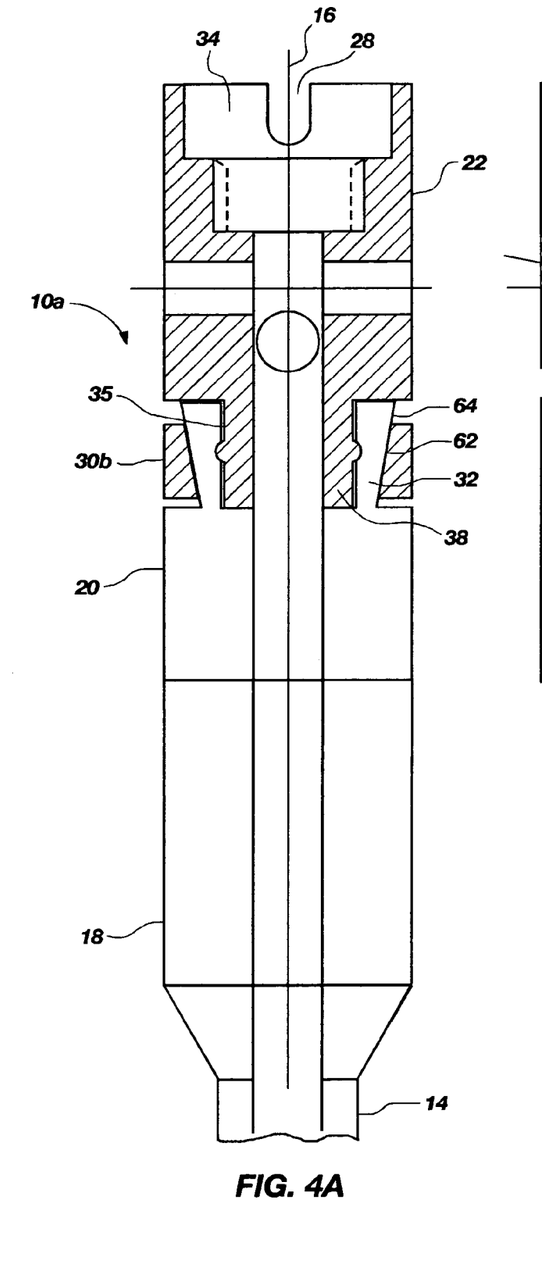
FIG. 4A is a side, cross-sectional break-away view of a further alternative embodiment of the intramedullary nail of FIG. 2A.
Figure 4B:
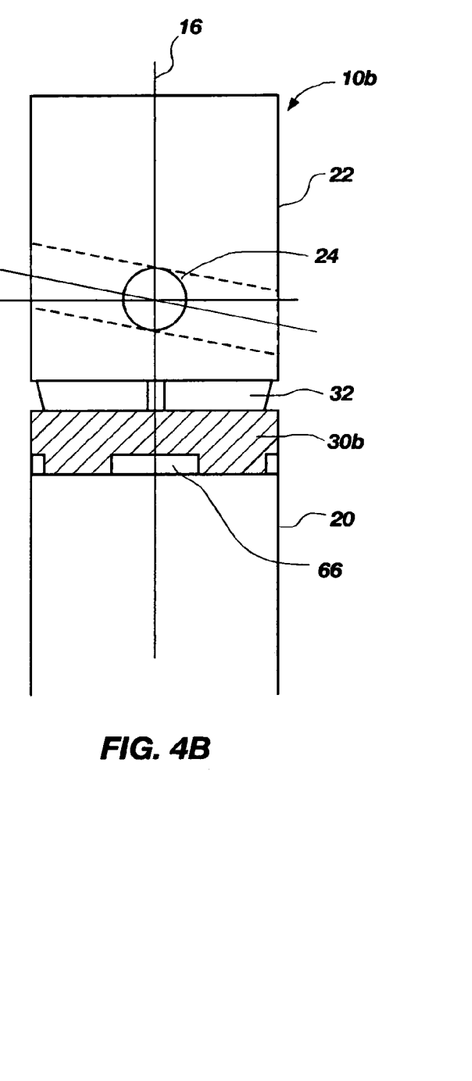
FIG. 4B is a side, break-away view of the intramedullary nail of FIG. 4A.

Reference will now to made to FIGS. 4A–4B to describe a third embodiment of the present invention. As previously discussed, the presently disclosed embodiments of the invention illustrated herein are merely exemplary of the possible embodiments of the invention, including that illustrated in FIGS. 4A–4B.

It will be appreciated that the third embodiment of the invention illustrated in FIGS. 4A–4B contains many of the same structures represented in FIGS. 1–3 and only the new or different structures will be explained to most succinctly explain the additional advantages which come with the embodiments of the invention illustrated in FIGS. 4A–4B. The third embodiment of the intramedullary nail 10*b* may include the locking ring 30*b* without threads. The locking ring 30*b* may include a tapered interior surface 62 that corresponds with a tapered exterior surface 64 of the sidewall 32. The locking ring 30*b* may also include one or more tool slots 66 for inserting a tool such as a screw driver or other form of a lever, to force the locking ring 30*b* axially over the sidewall 32. As the locking ring 30*b* moves axially over the sidewall 32, the locking ring 30*b* squeezes the sidewall 32. The squeezing interaction of the tapered interior surface 62 of the locking 30*b* with the tapered exterior surface 64 of the sidewall 32 causes the sidewall 32 to deflect inwardly toward the axis 16 to lock the connector 38 within the chamber 35.

The upper or third segment 22 may also include a notch 28 for receiving a tool (not shown) to rotate the third segment 22 or otherwise manipulate the nail 10, or for attaching an alignment guide or jig to facilitate locating the transverse openings 24.

Reference will now to made to FIGS. 5A–7B to describe a fourth embodiment of the present invention. As previously discussed, the embodiments of the invention illustrated herein are merely exemplary of the possible embodiments of the invention, including that illustrated in FIGS. 5A–7B.

It will be appreciated that the fourth embodiment of the invention illustrated in FIGS. 5A–7B contains many of the same structures represented in FIGS. 1–4 and only the new or different structures will be explained to most succinctly explain the additional advantages which come with the embodiments of the invention illustrated in FIGS. 5A–7B. The fourth embodiment intramedullary nail 10c may include a recess 68 formed on the connector 38. The recess 68 may extend around the perimeter of the connector 38. Also, a pin 70 may be received in a support 72, such as a transverse through-bore in the sidewalls 32. It will be appreciated that a plurality of supports 72 may be provided for receiving pins 70 for use with a single recess 68. As such, the supports 72 may be placed on different sides of the connector 38 as shown in FIG. 6A.

Figure 7A:
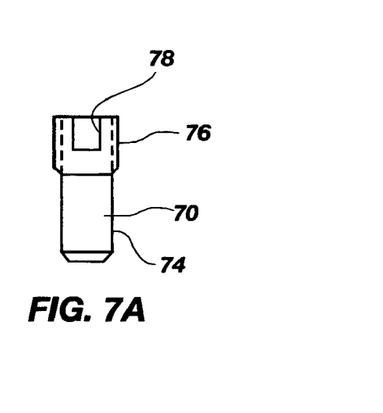
FIG. 7A is an enlarged side view of a pin of FIGS. 5–6.
Figure 7B:
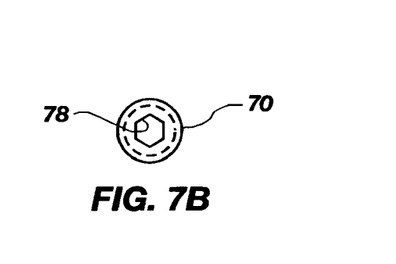
FIG. 7B is a top view of the pin of FIG. 7A.

As shown most clearly in FIG. 7A, the pin 70 may have a reduced diameter portion 74, and an enlarged diameter portion 76. The enlarged diameter portion 76 may be threaded to engage with corresponding threads in the support 72. The pin 70 may also have a driving surface 78, such as a polygonal surface or slot for example, for receiving a tool to apply a force to the pin 70 to rotate the pin 70 and drive the pin 70 into the support 72.

It will be understood that the recess 68 may be configured to receive the reduced diameter portion 74 of the pin 70. However, the enlarged diameter portion 76 of the pin 70 may not fit within the recess 68. An edge 73, as shown in FIG. 6A, may be formed on the connector 38 for engaging with the enlarged diameter portion 76 of the pin 70. Accordingly, when the pin 70 is placed in the support 12 such that the reduced diameter portion 74 is received within the recess 68, the connector 38 may be able to rotate about the longitudinal axis 16 with respect to the pin 70. Whereas, when the pin 70 is driven into the support 72 such that the enlarged diameter portion 76 is in contact with the edge 73 of the connector 38, the contact between the, enlarged diameter portion 76 and the edge 73 may prevent the connector 38 from rotating with respect to the pin 70 and support 72. Accordingly, the connector 38 may be locked in place.

Figure 5A:
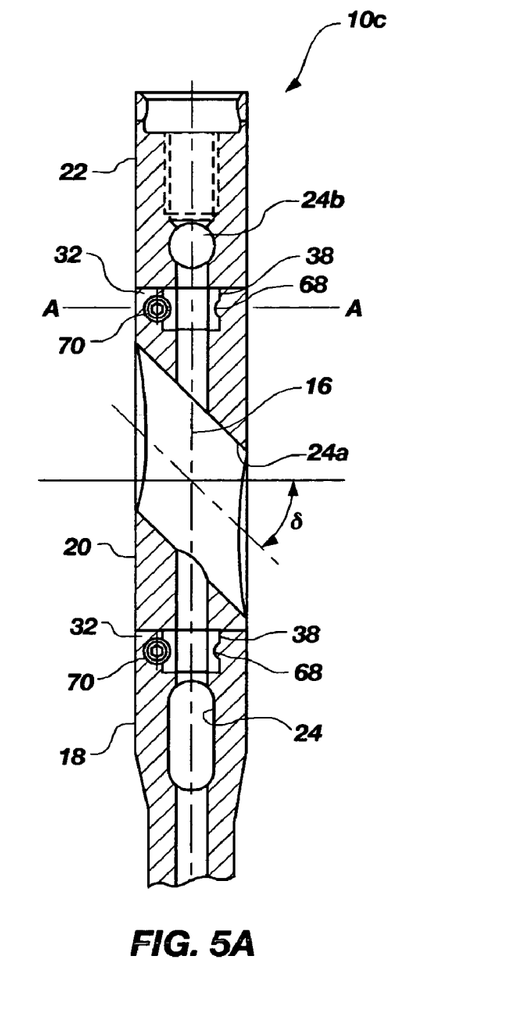
FIG. 5A is a side, cross-sectional break-away view of an additional embodiment of the intramedullary nail.
Figure 5B:
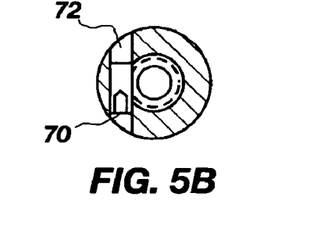
FIG. 5B is a top, cross-sectional view of the intramedullary nail of FIG. 5A, as viewed from line A—A.
Figure 5C:
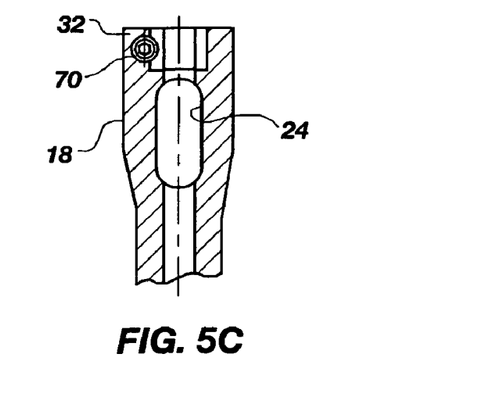
FIG. 5C is a side, cross-sectional break-away view of a first segment of the intramedullary nail of FIG. 5A.
Figure 5D:
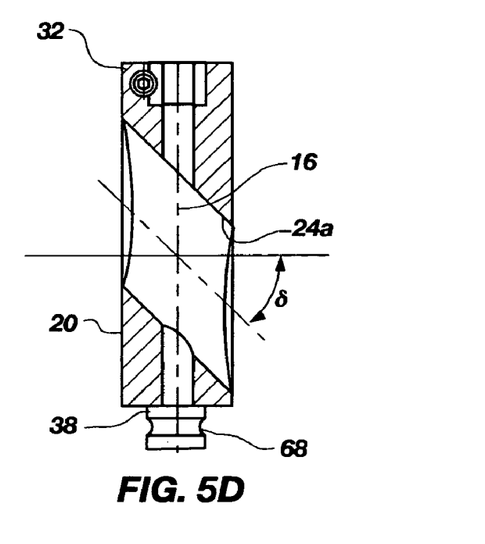
FIG. 5D is a side, cross-sectional view of a second segment of the intramedullary nail of FIG. 5A.
Figure 5E:
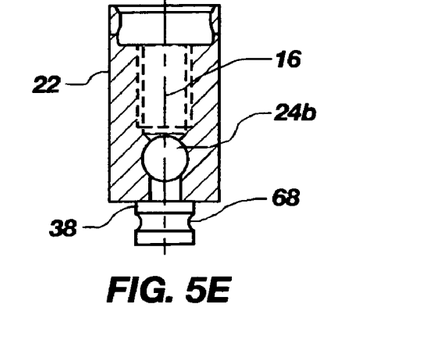
FIG. 5E is a side, cross-sectional view of a third segment of the intramedullary nail of FIG. 5A.
Figure 6A:
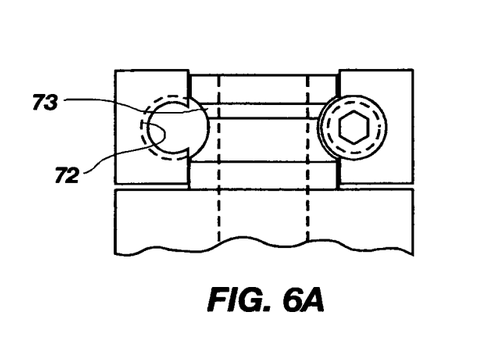
FIG. 6A is a side, cross-sectional break-away view of a further embodiment of the intramedullary nail.
Figure 6B:
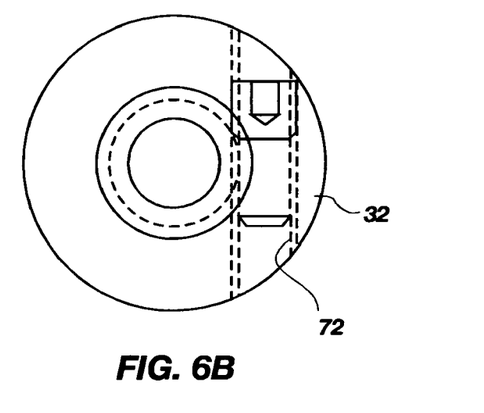
FIG. 6B is a top view of an additional embodiment of an intramedullary nail.

It will also be understood that the present invention may include angled transverse openings 24a, formed at various angles δ that may be offset from perpendicular to the longitudinal axis 16, as clearly shown in FIGS. 5A and 5D. Moreover, the present invention may include rounded transverse openings 24b which may extend perpendicularly to the longitudinal axis 16, or at an angle non-perpendicular to the longitudinal axis 16. The openings 24, 24a, 24b may or may not include inserts 48. The embodiment of the intramedullary nail 10c shown in FIG. 5A illustrates the first segment 18 having an oblong opening 24, the second segment 20 having an angled opening 24a, and the third segment 22 having a rounded opening 24b. However, it will be appreciated that each of the segments may have an oblong opening 24, an angled opening 24a or a rounded opening 24b. Accordingly, any combination of oblong openings 24, angled openings 24a or a rounded openings 24b may be used within the scope of the present invention.

It will be appreciated that the pins 70 may be released so that the segments can be rotated about the axis 16 again to readjust the angular position of the transverse openings 24 if necessary. It will also be appreciated that pins 70, the supports 72, and the recesses 68 may form part of a means for locking a segment.

Referring now to FIGS. 8A–8H, a fifth embodiment of the present invention is shown. As previously discussed, the presently described embodiments of the invention are merely exemplary of the possible embodiments of the invention, including that illustrated in FIGS. 8A–8H.

It will be appreciated that the fifth embodiment of the invention illustrated in FIGS. 8A–8H contains many of the same structures represented in FIGS. 1–7 and only the new or different structures will be explained to most succinctly explain the additional advantages which come with the embodiments of the invention illustrated in FIGS. 8A–8H. The fifth embodiment of the intramedullary nail 10d may include a first attachment element 80. The first attachment element 80 may include a threaded shaft 82 and a head 84. The head 84 may have an attachment element driving surface 86 in the form of a slot or some other engagement surface configured for receiving a driving tool (not shown) for driving the first attachment element 80. The first attachment element 80 may also include a bore 88 extending through the head 84 and the shaft 82.

Figures 8A, 8B, 8C, 8D, 8E, 8F, 8H:
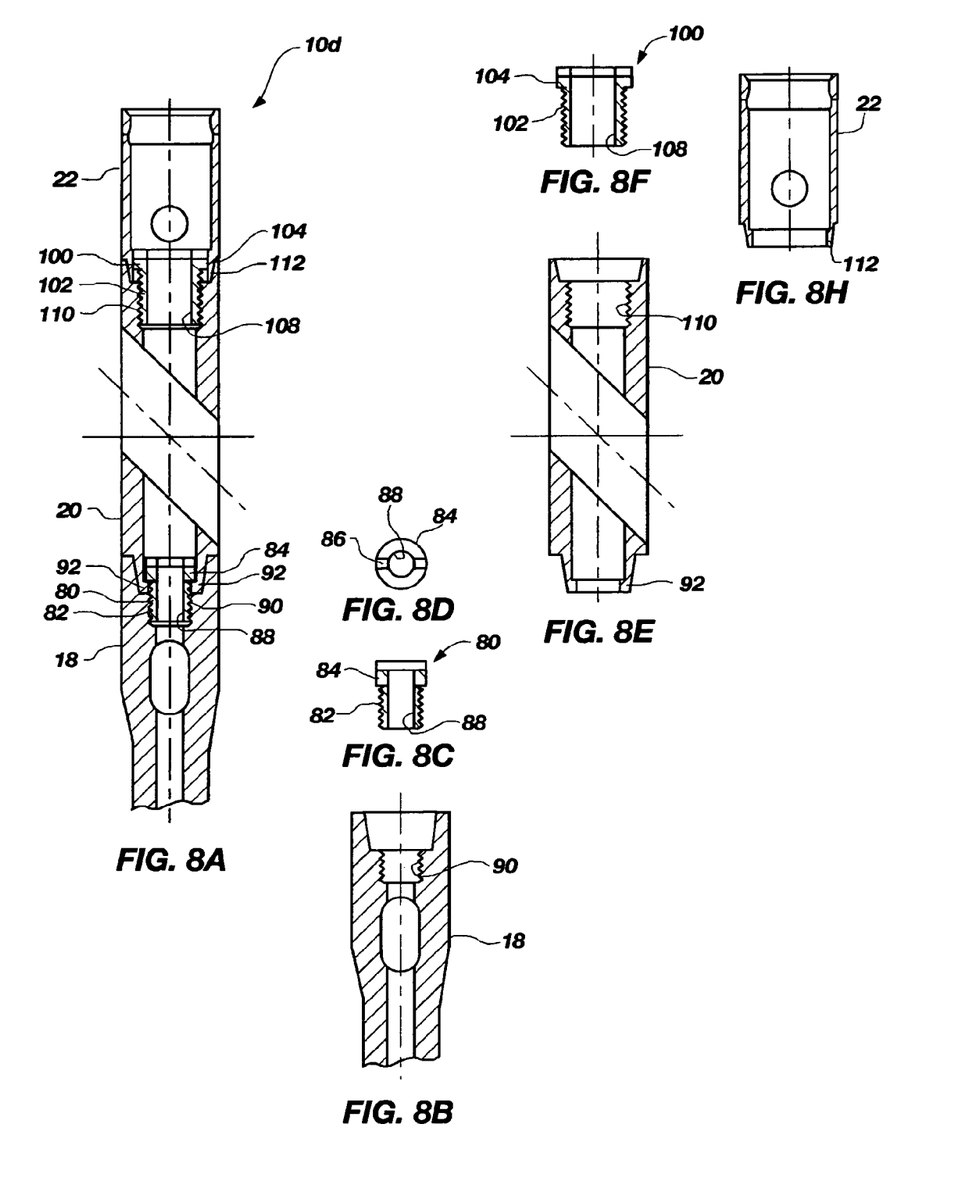
FIG. 8A is a side, cross-sectional break-away view of an additional embodiment of the intramedullary nail.
FIG. 8B is a side, cross-sectional break-away view of a first segment of the intramedullary nail of FIG. 8A.
FIG. 8C is a side, cross-sectional view of an attachment element used with the intramedullary nail of FIG. 8A.
FIG. 8D is a top view of the attachment element of FIG. 8C.
FIG. 8E is a side, cross-sectional view of a second segment of the intramedullary nail of FIG. 8A.
FIG. 8F is a side, cross-sectional view of an additional attachment element used with the intramedullary nail of FIG. 8A.
FIG. 8H is a side, cross-sectional view of a third segment of the intramedullary nail of FIG. 8A.
Figure 8G:
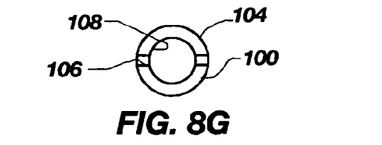
FIG. 8G is a top view of the attachment element of FIG. 8F.

The first segment 18 may include a threaded surface 90 for receiving the threaded shaft 82 of the first attachment element 80. The second segment 20 may include a shoulder 92 for abutting with the head 84. The first attachment element 80 may be received in the second segment 20 and may be rotated to engage the threaded shaft 82 with the threaded surface 90 of the first segment 18. The second segment 20 may be allowed to rotate with respect to the first segment 18 until the first attachment element 80 is tightened securely to the first segment 18. Once the first attachment element 80 is tightened, the second segment 20 may be prevented from rotating with respect to the first segment.

The intramedullary nail 10d of the fifth embodiment may also include a second attachment element 100 having a threaded shaft 102, a head 104, a driving surface 106, and a bore 108 similar to the first attachment element 80. The second segment 20 may also have a threaded surface 110, and the third segment 22 may have a have a shoulder 112. A driving tool may be inserted in the driving surface 106 to rotate the second attachment element 100 to engage the threaded shaft 102 with the threaded surface 110. The third segment 22 may be allowed to rotate with respect to the second segment 20 until the second attachment element 100 is tightened. It will be appreciated that as the second attachment element 100 is tightened, a frictional engagement between the shoulder 112 and the head 104 may prevent movement of the third segment 22 with respect to the head 104, in a similar fashion as that discussed above for the first attachment element 80.

It will be understood that the bore 108 may be sized such that a driving tool may be passed through the bore 108 so that the first attachment element 80 may be tightened or loosened in any sequential order with respect to the second attachment element 100. It will also be understood that the concepts of the present invention may be used with any number of segments and attachment elements.

Figure 9A:
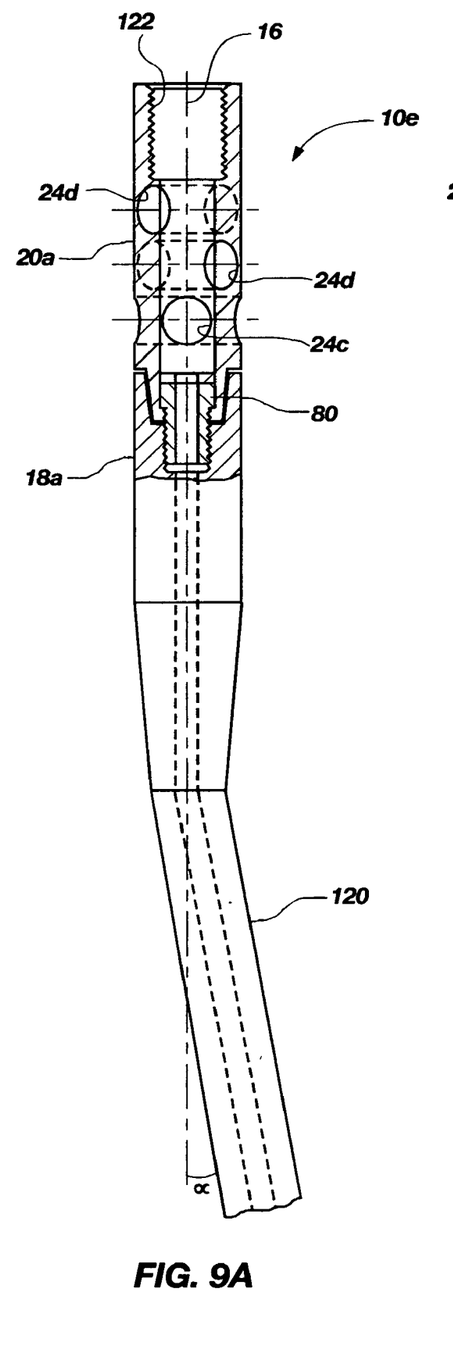
FIG. 9A is a side, cross-sectional break-away view of an additional embodiment of the intramedullary nail.
Figure 9B:
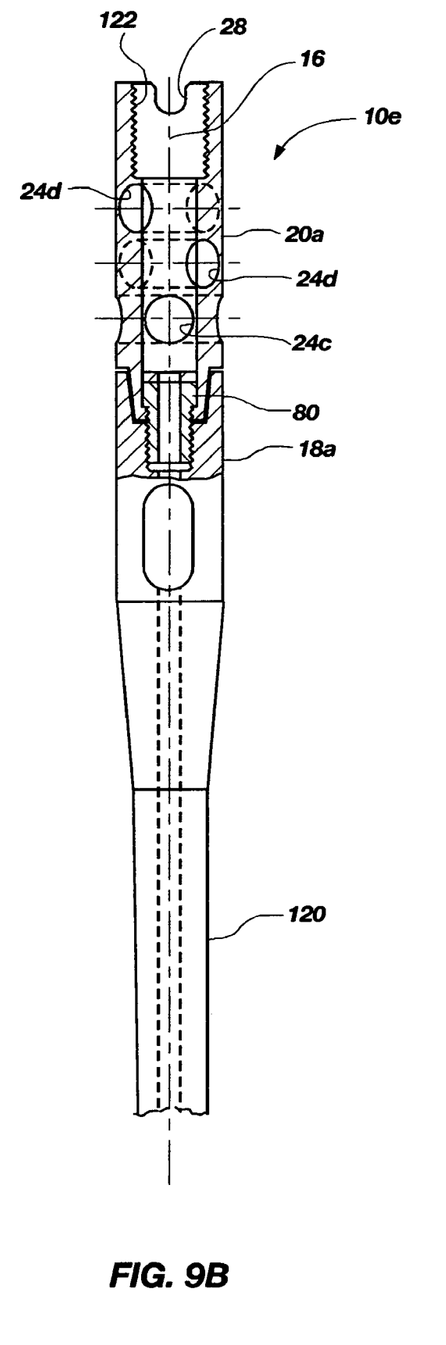
FIG. 9B is a side, cross-sectional break-away view of the intramedullary nail of FIG. 9A rotated by ninety degrees.

Referring now to FIGS. 9A–9B, a sixth embodiment of the present invention is provided. As previously discussed, the presently preferred embodiments of the invention illustrated herein are merely exemplary of the possible embodiments of the invention, including that illustrated in FIGS. 9A–9B.

It will be appreciated that the sixth embodiment of the invention illustrated in FIGS. 9A–9B contains many of the same structures represented in FIGS. 1–8 and only the new or different structures will be explained to most succinctly explain the additional advantages which come with the embodiments of the invention illustrated in FIGS. 9A–9B. The sixth embodiment of the intramedullary nail 10e may include an angled distal portion 120 for use with particular long bones such as the humerus and tibia, for example. The angled distal portion 120 may form an angle α with respect to the longitudinal axis 16 of up to approximately 10 degrees. It will be understood that various angles α may be used within the scope of the present invention. Moreover, the distal portion may be bowed to form a curved configuration rather than a bent configuration forming an angle.

Also, as depicted in FIGS. 9A and 9B, the intramedullary nail 10e may have only two segments, a first segment 18a, and a second segment 20a. The second segment 20a may include a plurality of transverse openings, including intersecting openings 24c and diagonal openings 24d. It will be understood that the intersecting openings 24c and the diagonal openings 24d may be rounded, or oblong, and they may be disposed at a perpendicular or non-perpendicular angle with respect to the longitudinal axis 16. Moreover, any number of openings may be formed in the segments. The second segment 20a may be rotatable about the longitudinal axis 16 and may be fixed against rotation with a first attachment element 80 as discussed above, or any other means for locking a segment as discussed herein.

The intramedullary nail 10e may also include a threaded chamber 122 as well as a notch 28 for attaching an alignment guide or jig to facilitate locating the transverse openings 24 or positioning the intramedullary nail 10e.

In summary, the present invention is directed to an adjustable intramedullary nail 10–10e for use in stabilizing a fracture until healing has occurred. The adjustable intramedullary nail 10–10e of the present invention includes an elongated nail member having a distal portion 14 and a proximal portion 12. The proximal portion 12 may be comprised of one or more rotating segments that can rotate 360 degrees about the nail axis 16. Each segment can be locked in its chosen position by the use of means for locking the segment such as a ring 30 or sleeve that may be threaded. Each segment may also contain one or more holes or transverse openings 24—24d for receiving for bone screws 26. Each segment may also contain slotted holes that may be filled with a bioabsorbable material that allows the surgeon to drill through the material for placement of a bone screw 26.

The internal locking mechanism may be formed in various configurations such as a threaded side wall that is allowed to collapse circumferentially due to two or more radial slits 37 positioned around the internal sleeve or sidewall 32. The adjustable nail 10 may be manufactured from a material that has a natural tendency to gall/friction weld. Therefore, when the internal thread is locked into position the mating surfaces gall/friction weld and permanently lock. Once locked into position it may not be possible to free the proximal segments to allow for axial rotation. The adjustable nail may be supplied pre-assembled with the threaded locking sleeves 30 in an unlocked position. Once the surgeon has selected the required orientation of the proximal screw holes 24 for the type of long bone fracture, the threaded locking sleeves 30 may be rotated in a clockwise direction using a wrench until the proximal segments are completely locked.

It will be appreciated that the locking rings 30, 30a, and 30b may be released in some embodiments so that the segments can be rotated about the axis 16 again to readjust the angular position of the transverse openings 24 if necessary. It will also be appreciated that the structure discussed herein including portions of the connector 38, the chamber 35, the locking rings 30, the pins 70 and the attachment elements 80, 100 may form embodiments of a means for locking a segment.

It will be appreciated that the structure and apparatus disclosed herein is merely exemplary of a means for locking a segment, and it should be appreciated that any structure, apparatus or system for locking a segment which performs functions the same as, or equivalent to, those disclosed herein are intended to fall within the scope of a means for locking a segment, including those structures, apparatus or systems for locking a segment which are presently known, or which may become available in the future. Anything which functions the same as, or equivalently to, a means for locking a segment falls within the scope of this element.

In accordance with the features and combinations described above, a useful method of treating a fractured bone includes the steps of:

(a) aligning a distal portion of a nail for positioning in a fractured bone;

(b) rotating a segment on a proximal portion of the nail to orient a bone screw opening along a desired insertion path of a bone screw;

(c) locking the segment with respect to the nail to prevent further rotation of the segment; and (d) inserting a bone screw through one of multiple possible angular positions in the bone screw opening to fix the nail to the bone.

Those having ordinary skill in the relevant art will appreciate the advantages provided by the features of the present invention. For example, it is a feature of the present invention to provide an intramedullary nail that is simple in design and manufacture. Another feature of the present invention is to provide such an intramedullary nail having segments with transverse openings that are angularly adjustable to treat fractured bone fragments having different configurations. It is a further feature of the present invention, in accordance with one aspect thereof, to provide an intramedullary nail that has adjustable segments that are capable of being locked in place and that can be unlocked to be readjusted.

In the foregoing Detailed Description, various features of the present invention are grouped together in single embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description of the Invention by this reference, with each claim standing on its own as a separate embodiment of the present invention.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A nail comprising:
   a proximal portion and a distal portion, said proximal portion and said distal portion defining a longitudinal axis, wherein said proximal portion comprises a plurality of segments along said longitudinal axis, each of said plurality of segments having an opening;
   wherein at least one of said plurality of segments is rotatable with respect to said distal portion about said longitudinal axis;
   wherein the nail comprises an insert in at least one of the openings for supporting a bone screw.

2. The nail of claim 1, wherein said plurality of segments comprise a first segment, a second segment, and a third segment.

3. The nail of claim 2, wherein said first segment is non-rotatably attached to said distal portion of said nail.

4. The nail of claim 2, wherein the first segment and the second segment each comprise a sidewall defining a chamber.

5. The nail of claim 4, wherein the sidewalls comprise a tapered exterior surface.

6. The nail of claim 4, wherein the second segment and the third segment each comprise a connector for being received in said chamber.

7. The nail of claim 6, wherein the sidewalls comprise a plurality of slits for allowing the sidewalls to deflect.

8. The nail of claim 6, further comprising a projection on an exterior surface of the connectors, and a groove on an interior surface of the sidewalls to provide an interference fit between the sidewalls and the connectors.

9. The nail of claim 1, further comprising means for locking said at least one rotatable segment for preventing said at least one rotatable segment from rotating with respect to said distal portion.

10. The nail of claim 1, wherein the nail further comprises a notch disposed on a proximal end for receiving a tool.

11. The nail of claim 1, wherein at least one of said openings in said plurality of segments is disposed at a non-perpendicular angle with respect to said longitudinal axis.

12. The nail of claim 1, wherein the openings each comprise a substantially oval shape to allow a bone screw to be inserted into the openings in a range of angles with respect to the longitudinal axis.

13. The nail of claim 1, wherein at least one of said plurality of segments comprises a connector having a recess, and wherein a pin is receivable in said recess to prevent said connector from rotating with respect to said pin.

14. The nail of claim 13, wherein said pin comprises a reduced diameter portion and an enlarged diameter portion, and wherein said enlarged diameter portion comprises threads.

15. The nail of claim 1, further comprising a first attachment element for preventing said at least one segment from rotating with respect to said distal portion.

16. The nail of claim 15, wherein said plurality of segments comprises a first segment having a threaded surface and a second segment having a shoulder, and wherein said first attachment element comprises a head and a threaded shaft such that said threaded shaft is configured to engage with said threaded surface and said head is configured to abut said shoulder to prevent said second segment from rotating with respect to said first segment.

17. The nail of claim 1, wherein said distal portion is formed at an angle with respect to said longitudinal axis of up to approximately 10 degrees.

18. A nail comprising:
   a proximal portion and a distal portion, said proximal portion and said distal portion defining a longitudinal axis, wherein said proximal portion comprises a plurality of segments along said longitudinal axis, each of said plurality of segments having an opening;
   wherein at least one of said plurality of segments is rotatable with respect to said distal portion about said longitudinal axis;
   wherein said nail further comprises means for locking said at least one rotatable segment for preventing said at least one rotatable segment from rotating with respect to said distal portion; and
   wherein said means for locking said at least one rotatable segment comprises a locking ring.

19. The nail of claim 18, wherein said locking ring comprises a threaded interior surface.

20. The nail of claim 18, wherein said locking ring comprises a tapered interior surface for creating a taper lock.

21. The nail of claim 18, wherein said locking ring comprises one or more tool openings for receiving a tool to apply a force to the locking ring.

22. The nail of claim 18, wherein the locking ring comprises a polygonal shape to facilitate applying a torque to the locking ring.

23. A nail comprising:
   a proximal portion and a distal portion, said proximal portion and said distal portion defining a longitudinal axis, wherein said proximal portion comprises a plurality of segments along said longitudinal axis, each of said plurality of segments having an opening;
   wherein at least one of said plurality of segments is rotatable with respect to said distal portion about said longitudinal axis;
   wherein said plurality of segments comprise a first segment, a second segment, and a third segment;
   wherein the first segment and the second segment each comprise a sidewall defining a chamber;
   wherein the second segment and the third segment each comprise a connector for being received in said chamber; and
   wherein the connectors each comprise a ledge, and the chambers each comprise a slot for receiving the ledge.

24. A nail comprising:
   a proximal portion and a distal portion, said proximal portion and said distal portion defining a longitudinal axis, wherein said proximal portion comprises a plurality of segments along said longitudinal axis, each of said plurality of segments having an opening;
   wherein at least one of said plurality of segments is rotatable with respect to said distal portion about said longitudinal axis;
   wherein said plurality of segments comprise a first segment, a second segment, and a third segment;
   wherein the first segment and the second segment each comprise a sidewall defining a chamber; and
   wherein the sidewalls comprise a threaded exterior surface.

25. An intramedullary nail for treating bone fractures, said intramedullary nail comprising:
   a proximal portion and a distal portion, said proximal portion and said distal portion defining a longitudinal axis, wherein said proximal portion comprises at least one segment that is rotatable with respect to said distal portion about said longitudinal axis; and
   means for locking said at least one segment for preventing said at least one segment from rotating with respect to said distal portion;
   wherein said means for locking said at least one segment comprises a locking ring.

* * * * *